US006849585B1

(12) United States Patent
Farrell et al.

(10) Patent No.: US 6,849,585 B1
(45) Date of Patent: Feb. 1, 2005

(54) BAR WITH GOOD USER PROPERTIES COMPRISING ACID-SOAP COMPLEX AS STRUCTURANT AND LOW LEVELS OF SYNTHETIC

(75) Inventors: Terence James Farrell, Tenafly, NJ (US); Charles Craig Nunn, Rutherford, NJ (US)

(73) Assignee: Unilever Home & Personal Care USA, a division of Conopco, Inc., Greenwich, CT (US)

( * ) Notice: Subject to any disclaimer, the term of this patent is extended or adjusted under 35 U.S.C. 154(b) by 0 days.

(21) Appl. No.: 10/756,615

(22) Filed: Jan. 13, 2004

(51) Int. Cl.[7] .................................................. A61K 7/50

(52) U.S. Cl. ....................... 510/152; 510/153; 510/151; 510/155

(58) Field of Search ................................. 510/141, 151, 510/152, 153, 155

(56) References Cited

U.S. PATENT DOCUMENTS 3,989,647 A 11/1976 Prince
3,991,001 A 11/1976 Srivivasan et al.
4,673,525 A 6/1987 Small et al.
4,695,395 A 9/1987 Caswell et al.
4,812,253 A 3/1989 Small et al.
4,832,861 A 5/1989 Resch
4,954,281 A 9/1990 Resch
5,006,529 A 4/1991 Resch
5,076,953 A 12/1991 Jordan et al.
5,204,014 A 4/1993 Redd et al.
5,225,097 A 7/1993 Kacher et al.
5,225,098 A 7/1993 Kacher et al.
5,262,079 A * 11/1993 Kacher et al. .............. 510/146
5,387,362 A * 2/1995 Tollens et al. .............. 510/151
5,540,852 A * 7/1996 Kefauver et al. ........... 510/152
5,543,072 A 8/1996 Fost et al.
5,661,120 A 8/1997 Finucane et al.
5,681,980 A 10/1997 Beerse et al.
5,945,389 A 8/1999 Richard et al.
6,069,121 A 5/2000 Cassady et al.
6,143,704 A * 11/2000 Van Gunst et al. ......... 510/152
6,218,348 B1 4/2001 Aronson et al.
6,242,394 B1 6/2001 Chamberlin, III
6,242,399 B1 * 6/2001 Chambers et al. .......... 510/154

OTHER PUBLICATIONS

U.S. Appl. No. 10/756,616, filed Jan. 13, 2004, Farrell et al., J6878(C), Fatty Acid Soap/Fatty Acid Bars Which Process and Have Good Lather.

U.S. Appl. No. 10/756,617, filed Jan. 13, 2004, Kerschner et al., J6880(C), Compositions and Process for Preparing Cleansing Bars Comprising Low Levels of Soluble Surfactant for Enhanced Fragrance Deposition/Longevity.

* cited by examiner

*Primary Examiner*—Necholus Ogden
(74) *Attorney, Agent, or Firm*—Ronald A. Koatz

(57) ABSTRACT

The invention relates to soap/free fatty acid bars in which high amounts of free fatty acid (i.e., greater than 35%, preferably greater than 40% and ratio of FFA to soap greater than 1:1) and low levels of synthetic may be used. In the bar, the free fatty acid is believed to form a complex which is believed to act as a structurant, thereby allowing less use of synthetic surfactant. The bar should require less synthetic surfactant. Total amount of unsaturated material in soap and fatty acid should be no higher than 15%

In a second embodiment of the invention, the bar may be made by a neutralization process whereby fatty acid is combined with caustic (e.g., lower than 50% caustic) to form soap and free fatty acid in defined amounts or proportions.

8 Claims, No Drawings

BAR WITH GOOD USER PROPERTIES COMPRISING ACID-SOAP COMPLEX AS STRUCTURANT AND LOW LEVELS OF SYNTHETIC

FIELD OF THE INVENTION

The present invention relates to soap/fatty acid based bars having high levels of free fatty acid (e.g., greater than 35%, preferably greater than 36%, more preferably greater than 38%, even more preferable greater than 40% or greater than 41% by wt.); low level of synthetic surfactant (e.g. less than 25%, preferably less than 20% by wt.), while retaining good user properties (e.g. foam).

BACKGROUND OF THE INVENTION

Bars based on synthetic surfactant ("syndet" bars) and having some fatty acid soap are known. Syndet bars have levels of synthetic surfactant well beyond those of the invention.

Fatty acid soap bars containing some synthetic surfactant are also known in the art. Such bars may contain free fatty acid (superfat), although generally (though not necessarily) not at levels where free fatty acid (FFA) level is greater than that of soap. The art fails to disclose that in bars with high fatty acid/soap, low synthetic, the total level of unsaturated soap can be no more than a defined amount.

When additional free fatty acid is added to either fatty acid soap or synthetic soap bars, this additional free fatty acid is known as "superfat". It is generally added to provide benefits such as a richer, creamier lather. The well known Dove® bar, for example, contains about 20% free fatty acid. Dove® has levels of synthetic far higher than levels used in the subject invention.

Generally, it is important to limit the upper level of free fatty acid (FFA) used in a bar for a variety of reasons. For example, since FFA is hydrophobic, use of high amounts would be expected to decrease the ability of a bar to foam or lather.

Unexpectedly, applicants have found that when FFA acid is added in much greater amounts (in one embodiment of the invention it is added to the bar composition using an under-neutralization process as disclosed herein), the bar will still retain excellent foaming properties. While not wishing to be bound by theory, this is believed to occur because the acid-soap microstructure of the bar which develops (for example, due to underneutralization when this process is used) has enough integrity to be initially extruded, but that integrity wears away upon washing efficiently enough to provide sufficient lather (i.e., from the soap/free fatty acid), even though minimal amounts of surfactant are used. That is, it is believed that an acid-soap complex initially acts as a structurant (which does not defoam) and that as the structure breaks down, it allows good lathering during the wash process. At the same time, since it is acting as a structuring complex, far less synthetic is needed (e.g., for foaming) than might previously have been believed.

The bars thus comprises a minimum of about 65% of a combination of fatty acid soap and FFA; less than about 25% (preferably, at least about 10%) synthetic surfactant and from 1 to about 15%, preferably 2 to 14% (less than 15%) water. In a preferred embodiment, the level of FFA is equal to or more preferably greater than the level of soap. Preferred levels of free fatty acid is greater than about 40% by weight. The bars are generally, although not necessarily (e.g., may be melt cast or frame cooling process) prepared by an extrusion process and the bar will lather at least 50 ml using standard bar appraisal technique or BLAM.

As noted, high levels of free fatty acid (e.g., above about 35%, preferably above 40%) are preferred as is ratio of FFA to soap of 1:1 or preferably higher. Further, levels of synthetic are low. Dove® bars contain about 20% FFA and much higher levels of synthetic. In our invention, the level of FFA is also preferably higher than the level of synthetic used. Also in our invention, the level of water should be higher than 5% by weight but lower than about 14% by weight, preferably less than about 12% by weight.

U.S. Pat. No. 3,989,647 to Prince discloses bars containing up to about 35% by wt. fatty acid and at least 40% non-soap surfactant. The bars of the subject invention generally contain above about 35% FFA and also contain much lower levels of synthetic (i.e., below about 25% by wt.).

U.S. Pat. No. 4,673,525 to Small et al. discloses bars containing 20–70%, preferably 40–70% synthetic surfactant, up to 40% "moisturizer" (which is preferably not fatty acid) and up to 25% soap. The ratio of synthetic to soap is 2:1 to 12:1. In the subject application, the level of soap generally exceeds the level of synthetic and the synthetic to soap ratio never approaches 2:1.

U.S. Pat. No. 4,695,395 to Caswell discloses bars comprising soap, sodium isethionate, FFA and acyl isethionate. The amount of FFA is up to 25% (see claim 3). Levels of FFA in the subject invention are higher.

U.S. Pat. No. 4,832,861 to Resch discloses bars which may comprise 30 to 70% soap and 1 to 40% FFA (e.g., stearic acid). From the examples, it is clear the bars are predominantly soap bars with cocoyl isethionate and relatively smaller amounts of FFA. The subject invention comprises much higher FFA. Further, the subject application requires hardness of extruded bar of at least 90, preferably at least 100 kPa as measured by cheese wire method and it is not clear that bars of Resch would need such limitation. Indeed, given high levels of salt used in Resch, it may well be that many of the bars would likely not be this hard.

U.S. Pat. No. 5,225,097 to Kacher et al. discloses skin pH freezer bars requiring at least 15% water.

U.S. Pat. No. 5,661,120 to Finucane discloses bars with up to 35% FFA and up to 25% soap. The subject invention requires at least 65% combination soap and 6 FFA.

U.S. Pat. No. 6,218,348 to Aronson discloses bars comprising fatty acid soap, up to 35% FFA, polyalkylene glycol of defined MW and salts of protic acid. From the specification and claims, it is clear the reference is concerned with bars that are predominantly (preferably 50–75% by wt.) fatty acid soap and lower amounts (preferably 2 to 14%) FFA.

Other patents of general interest include the following:

U.S. Pat. No. 3,991,001 to Srinivasan et al.;
U.S. Pat. No. 4,812,253 to Small et al.;
U.S. Pat. No. 4,954,281 to Resch;
U.S. Pat. No. 5,006,529 to Resch;
U.S. Pat. No. 5,076,953 to Jordan et al.;
U.S. Pat. No. 5,204,014 to Redd et al.;
U.S. Pat. No. 5,225,098 to Kacher et al.;
U.S. Pat. No. 5,543,072 to Fost et al.;
U.S. Pat. No. 5,681,980 to Beerse et al.;
U.S. Pat. No. 5,945,389 to Richard et al.;
U.S. Pat. No. 6,069,121 to Cassady et al.; and
U.S. Pat. No. 6,242,394 to Chambers et al.

In none of the patents of which applicants are aware is there disclosed bars where the level of FFA exceeds the level of soap; the level of syndet is below a certain level (below 25% but preferably at least 10% by wt.); and there is found an acid-soap complex. Specifically, the fatty acid and soap together comprise at least about 65%, preferably at least 66%, more preferably at least 68%, more preferably at least 70% of the bar and FFA is at least 35%, preferably at least 36%, more preferably at least 38% of bar, most preferably at least 40% and even more preferably above 40% by weight. Further, synthetic surfactant comprises less than about 25%, preferably less than about 23%, more preferably less than about 20% of composition and water comprises less than about 15%, preferably less than about 13%. The bars of the invention are preferably prepared by under-neutralizing free fatty acid during formation of an acid-soap complex.

BRIEF DESCRIPTION OF THE INVENTION

The present invention relates to bar compositions having low levels of synthetic (i.e., non-soap) surfactant, yet which are good foaming and not harsh to the skin. Benefits are accomplished using high levels of free fatty acid (preferably ratio of FFA to soap is equal or greater than 1:1; preferably FFA is greater than 35%, more preferably greater than 40% by weight of compositions) even though it might be expected that such high levels of FFA could lead to a loss of lather, increased wear, and/or enhanced harshness. It is believed that soap/fatty acid form a structuring network which allows less synthetic to be used but which complex later dissolves during wash and thereby allowing good foam properties unexpected from a high soap/FFA, low synthetic system.

Specifically, compositions of the invention comprise:

(1) at least about 65% by wt., preferably at least 66%, more preferably at least 68%, more preferably at least 70% mixture of fatty acid soap and free fatty acid wherein at least 35%, preferably at least 37%, more preferably at least 40% by wt. more preferably more than 40% by weight of bar is free fatty acid and wherein said fatty acid soap in the bar is preferably although not necessarily produced when FFA mixes with less than 50 mol % caustic (Also preferably the ratio of FFA to soap is at least 1:1 and preferably greater than 1:1);

(2) less than 25%, preferably less than 24%, more preferably less than 20% non-soap synthetic surfactant (preferably amount of the FFA is greater than level of synthetic);

(3) less than 15%, preferably less than 14% (e.g., 2–14%) water; wherein said bar has lather of at least 50 ml, measured by BLAM, as referenced test;

wherein said bar is preferably prepared by an extrusion process; and wherein the hardness of the extrusion bar is at least 90 kPa, preferably at least 100 kPa, as measured by cheese wire method.

DETAILED DESCRIPTION OF THE INVENTION

The present invention relates to bars having high levels of free fatty acid and soap (i.e., at least about 65% together, at least about 35% FFAs; preferably ratio of FFA to soap at level 1:1, more preferably greater than 1:1) preferably formed by under-neutralization (in mol % terms less than 50 mol % will result in underneutralization since 50 mol % caustic yields full neutralization, i.e., all soap and no free fatty acid) by the caustic used in soap formation process (e.g., NaOH) to form mixture of soap and FFA.

Specifically, together wt. % of free fatty acid and of soap formed from free fatty acid is at least 65%, preferably at least 66%, more preferably at least 68%, more preferably at least 70% of final bar composition; while wt. % of free fatty acid alone (a) is preferably greater than that of soap formed and (b) comprises at least 35%, preferably at least 36%, more preferably at least 38%, more preferably at least 40% of the final composition.

Without wishing to be bound by theory, the soap/free fatty acid is believed to form a soap-free fatty acid complex which structures the bar and therefore requires no more than 25% synthetic. It is believed the complex will disassociate during the wash and permit the bar to have foaming for greater than would be expected for a soap/FFA low synthetic bar.

As noted, conventionally it would be expected that hydrophobic free fatty acid would reduce foam (particularly the generally longer chain, generally $C_{12}$ and higher length molecules of the invention.

Because the complex is apparently acting as a structurant, it can also deliver synthetic surfactant and thus act as a means for using much lower synthetic surfactant level.

In short, the complex leads to formation of a low surfactant bar with excellent foaming and wear properties.

Process

In one embodiment, bars of the invention are made by an extrusion process wherein fatty acid is combined with caustic (or any molecule capable of supplying alkali or other metal to react with fatty acid to form soap) at a temperature of about 180° F. to 230° F.

The FA can be any $C_8$ to $C_{24}$, generally unbranched hydrocarbon. However, the total fatty acid (and a total final soap plus FA) should be no more than 15% total composition unsaturated.

As noted, one key aspect of the invention is that, even with high soap FFA, particularly FFA and low synthetic, the bar maintains good foaming, as measured by BLAM test described herein. The foam should be at least 50 ml. Preferably at least 55 ml, more preferably at least 60 ml.

The extruded bar will have a hardness of at least 90 kPa as measured by cheese wire method defined in protocol.

Except in the operating and comparative examples, or where otherwise explicitly indicated, all numbers in this description indicating amounts or ratios of materials or conditions or reaction, physical properties of materials and/or use are to be understood as modified by the word "about".

Where used in the specification, the term "comprising" is intended to include the presence of stated features, integers, steps, components, but not to preclude the presence or addition of one or more features, integers, steps, components or groups thereof.

The following examples are intended to further illustrate the invention and are not intended to limit the invention in any way.

Unless indicated otherwise, all percentages are intended to be percentages by weight. Further, all ranges are to be understood to encompass both the ends of the ranges plus all numbers subsumed within the ranges.

EXAMPLES

Protocol

Bar Lather Volume Assessment (BLAM)

Principle

To determine the volume of lather which can be generated and collected from a given bar formulation under a strict regiment of washing.

Apparatus

Toilet bars 2 large sinks

Measuring funnel

The measuring funnel is constructed by fitting a 10½inch diameter plastic funnel to a graduated cylinder which has had the bottom cleanly removed. Minimally the graduated cylinder should be 100 cc's. The fit between the funnel and the graduated cylinder should be snug and secure.

Procedure

Before evaluations proceed, place the measuring funnel into one of the sinks and fill the sink with water until the 0 cc mark is reached on the graduated cylinder.

i. Run the faucet in the second sink and set the temperature to 95° F. (35° C.).

ii. Holding the bar between both hands under running water, rotate the bar for ten (10) half turns.

iii. Remove hands and bar from under the running water.

iv. Rotate the bar fifteen (15) half turns.

V. Lay the bar aside.

vi. Work up lather for ten (10) seconds.

vii. Place funnel over hands.

viii. Lower hands and funnel into the first sink.

ix. Once hands are fully immersed, slide out from under funnel.

x. Lower the funnel to the bottom of the sink.

xi. Read the lather volume.

xii. Remove the funnel with lather from the first sink and rinse in the second sink.

The test should be performed on 2 bars of the same formulation, same batch etc. and the volume should be reported as an average of the 2 assessments.

Yield Stress Measure

The bars of the invention preferably have yield stress of at least 90 kPa, preferably 100 kPa measured using a cheese wire with a diameter of 0.5 milliliters and having a 200 gram weight attached.

Examples 1–14

Example 1–15 below disclose the weight % of the composition according to the invention, including description of molar ratio of soap/fatty acid.

| Molar Ratio of Soap/Fatty Acid | | |
|---|---|---|
| $C_{16}/C_{18}$ | $C_{18:1}$ | NaOH |
| 75 | 0 | 25 |
| Nominal Composition | | Weight % |
| Soap | | 24.9 |
| Fatty Acid | | 46.1 |
| SASOLFIN 23S* | | 20 |
| Water | | 9 |

BLAM value: 92
*alkyl sulfate sodium salt

| Molar Ratio of Soap/Fatty Acid | | |
|---|---|---|
| $C_{16}/C_{18}$ | $C_{18:1}$ | NaOH |
| 75 | 0 | 25 |
| Nominal Composition | | Weight % |
| Soap | | 22.6 |
| Fatty Acid | | 41.9 |
| SASOLFIN 23S | | 20 |
| Water | | 9 |
| Glycerine | | 5 |
| Perfume | | 1.5 |

BLAM value: 127

| Molar Ratio of Soap/Fatty Acid | | |
|---|---|---|
| $C_{16}/C_{18}$ | $C_{18:1}$ | NaOH |
| 75 | 0 | 25 |
| Nominal Composition | | Weight % |
| Soap | | 22.6 |
| Fatty Acid | | 41.9 |
| Alpha-Step PC 48 (Stepan)* | | 10 |
| Hostapon 85 | | 10 |
| Water | | 9 |

BLAM value: 75
*combination of sodium methyl-2 sulfo $C_{12}$–$C_{18}$ ester and disodium 2-sulfo $C_{12}$–$C_{18}$ fatty add (i.e., a partially neutralized fatty acid methyl ester).

| Molar Ratio of Soap/Fatty Acid | | |
|---|---|---|
| $C_{16}/C_{18}$ | $C_{18:1}$ | NaOH |
| 87.5 | 0 | 12.5 |
| Nominal Composition | | Weight % |
| Soap | | 10.8 |
| Fatty Acid | | 60.2 |
| Alpha-Step PC 48 (Stepan) | | 10 |
| Hostapon 85* | | 10 |
| Water | | 9 |

BLAM value: 62
*sodium cocoyl isethionate

| Molar Ratio of Soap/Fatty Acid | | |
|---|---|---|
| $C_{16}/C_{18}$ | $C_{18:1}$ | NaOH |
| 87.5 | 0 | 12.5 |
| Nominal Composition | | Weight % |
| Soap | | 12 |
| Fatty Acid | | 67 |
| Alpha-Step PC 48 (Stepan) | | 5 |
| Hostapon 85 | | 5 |
| Water | | 9 |
| Sodium LAS | | 2 |

BLAM value: 53

| Molar Ratio of Soap/Fatty Acid | | |
|---|---|---|
| $C_{16}/C_{18}$ | $C_{18:1}$ | NaOH |
| 75 | 0 | 25 |

| Nominal Composition | Weight % |
|---|---|
| Soap | 24.2 |
| Fatty Acid | 44.8 |
| Alpha-Step PC 48 (Stepan) | 10 |
| Hostapon 85 | 10 |
| Water | 9 |
| Sodium LAS | 2 |

BLAM value: 90

| Molar Ratio of Soap/Fatty Acid | | |
|---|---|---|
| $C_{16}/C_{18}$ | $C_{18:1}$ | NaOH |
| 87.5 | 0 | 12.5 |

| Nominal Composition | Weight % |
|---|---|
| Soap | 10.5 |
| Fatty Acid | 58.5 |
| Alpha-Step PC 48 (Stepan) | 10 |
| Hostapon 85 | 10 |
| Water | 9 |
| Sodium LAS | 2 |

BLAM value: 100

| Molar Ratio of Soap/Fatty Acid | | |
|---|---|---|
| $C_{16}/C_{18}$ | $C_{18:1}$ | 10:1 molar NaOH:KOH |
| 87.5 | 0 | 12.5 |

| Nominal Composition | Weight % |
|---|---|
| Soap | 8.6 |
| Fatty Acid | 60.4 |
| Hostapon 85 | 20 |
| Water | 9 |
| Sodium LAS | 2 |

BLAM value: 85

| Molar Ratio of Soap/Fatty Acid | | |
|---|---|---|
| $C_{16}/C_{18}$ | $C_{18:1}$ | 10:1 molar NaOH:KOH |
| 62.5 | 12.5 | 25 |

| Nominal Composition | Weight % |
|---|---|
| Soap | 23 |
| Fatty Acid | 46 |
| Hostapon 85 | 20 |
| Water | 9 |
| Sodium LAS | 2 |

BLAM value: 60

| Molar Ratio of Soap/Fatty Acid | | |
|---|---|---|
| $C_{16}/C_{18}$ | $C_{18:1}$ | NaOH |
| 75 | 0 | 25 |

| Nominal Composition | Weight % |
|---|---|
| Soap | 24.9 |
| Fatty Acid | 46.1 |
| Sodium N-cocoyl glycinate | 20 |
| Water | 9 |
| Perfume | 1 |

BLAM value: 95

| Molar Ratio of Soap/Fatty Acid | | |
|---|---|---|
| $C_{12}$ | $C_{18:1}$ | NaOH |
| 51 | 12.5 | 36.5 |

| Nominal Composition | Weight % |
|---|---|
| Soap | 54 |
| Fatty Acid | 36 |
| Water | 5 |
| SASOLFIN 23S | 5 |

BLAM value: 75

| Molar Ratio of Soap/Fatty Acid | | |
|---|---|---|
| $C_{16}/C_{18}$ | $C_{18:1}$ | NaOH |
| 75 | 0 | 25 |

| Nominal Composition | Weight % |
|---|---|
| Soap | 19.1 |
| Fatty Acid | 35.3 |
| Sodium cocoyl isethionate | 9.9 |
| Lauryl sulfosuccinate | 6.9 |
| Water | 8.9 |
| Sodium laureth sulfate | 6.9 |
| Glycerine | 4.9 |
| Cocamidopropyl betaine | 3.9 |
| Polyethylene glycol 1450 | 3 |
| Fragrance | 1.15 |

BLAM value: 112

| Molar Ratio of Soap/Fatty Acid | | |
|---|---|---|
| $C_{14}$ | $C_{18:1}$ | NaOH |
| 75 | 0 | 25 |

| Nominal Composition | Weight % |
|---|---|
| Soap | 25.14 |
| Fatty Acid | 45.86 |
| Water | 9 |
| SASOLFIN 23S | 20 |

BLAM value: 115

| Molar Ratio of Soap/Fatty Acid | | |
|---|---|---|
| $C_{12}$ | $C_{18.1}$ | NaOH |
| 63.5 | 0 | 36.5 |
| Nominal Composition | Weight % | |
| Soap | 54 | |
| Fatty Acid | 36 | |
| Water | 5 | |
| SASOLFIN 23S | 5 | |

BLAM value: 110

As seen, all examples have high levels of fatty acid (>35% m preferably >40%) and low level of synthetic. All examples lathered well as seen from the BLAM results. In addition, all bars extruded within defined hardness parameters.

What is claimed is:

1. A bar composition comprising:

(a) at least about 65% by wt. of a mixture of fatty acid soap and fatty acid, wherein greater than 40% by wt. of the bar is free fatty acid;

(b) less than 25% non-soap synthetic surfactant;

(c) less than 15% water;

where said bar lathers at least 50 ml measured by BLAM test; and wherein the hardness of the extruded bar is at least 90 kPa as measured by cheese wire method.

2. A composition according to claim 1, wherein less than 24% by wt. is synthetic surfactant.

3. A composition according to claim 2, wherein less than 20% by wt. is synthetic surfactant.

4. A composition according to claim 1, wherein there is at least 10% by wt. synthetic surfactant.

5. A composition according to claim 1, wherein bar lather is at least 55 ml.

6. A bar according to claim 1, wherein bar is formed by combining fatty acid with less than 50 mol. % caustic leaving soap and fatty acid.

7. A composition according to claim 1, wherein ratio of FFA to soap in final bar is at least 1:1.

8. A bar according to claim 1, having a hardness of at least 100 kPa.

* * * * *